United States Patent
Jørgensen et al.

(10) Patent No.: US 11,328,390 B2
(45) Date of Patent: May 10, 2022

(54) METHOD FOR ADAPTIVE DENOISING AND SHARPENING AND VISUALIZATION SYSTEMS IMPLEMENTING THE METHOD

(71) Applicant: AMBU A/S, Ballerup (DK)

(72) Inventors: Andreas Härstedt Jørgensen, Rødovre (DK); Finn Sonnenborg, Frederikssund (DK)

(73) Assignee: AMBU A/S, Ballerup (DK)

( * ) Notice: Subject to any disclaimer, the term of this patent is extended or adjusted under 35 U.S.C. 154(b) by 198 days.

(21) Appl. No.: 15/931,576

(22) Filed: May 13, 2020

(65) Prior Publication Data

US 2021/0358086 A1    Nov. 18, 2021

(51) Int. Cl.
| | |
|---|---|
| *G06T 5/00* | (2006.01) |
| *G06K 9/40* | (2006.01) |
| *A61B 1/00* | (2006.01) |
| *A61B 1/05* | (2006.01) |

(52) U.S. Cl.
CPC .......... *G06T 5/002* (2013.01); *A61B 1/00009* (2013.01); *A61B 1/05* (2013.01); *G06T 5/003* (2013.01); *G06T 2200/24* (2013.01); *G06T 2207/10016* (2013.01)

(58) Field of Classification Search
None
See application file for complete search history.

(56) References Cited

U.S. PATENT DOCUMENTS

| | | | |
|---|---|---|---|
| 5,432,869 A | * | 7/1995 | Matsumoto ............ H04N 9/646 348/607 |
| 6,665,448 B1 | | 12/2003 | Maurer |
| 6,956,602 B2 | | 10/2005 | Higuchi et al. |
| 8,199,223 B2 | | 6/2012 | Sasaki |
| 8,351,725 B2 | | 1/2013 | Pan et al. |
| 8,605,970 B2 | | 12/2013 | Bar-Aviv et al. |
| 8,711,234 B2 | | 4/2014 | Tzur et al. |
| 9,854,962 B2 | | 1/2018 | McGrail et al. |
| 10,321,804 B2 | | 6/2019 | Jacobsen et al. |
| 10,406,309 B2 | | 9/2019 | Daher |
| 10,478,054 B2 | | 11/2019 | Nave et al. |

(Continued)

FOREIGN PATENT DOCUMENTS

| | | |
|---|---|---|
| EP | 1698271 A1 | 9/2006 |
| EP | 3590414 A1 | 1/2020 |

OTHER PUBLICATIONS

OmniVision Technologies Inc., OV6930 Product Brief, 2 pgs., Oct. 2014.

(Continued)

*Primary Examiner* — Randolph I Chu
(74) *Attorney, Agent, or Firm* — Faegre Drinker Biddle & Reath LLP

(57) ABSTRACT

A visualization system including a video processing apparatus (VPA) including a processor; and memory having processing instructions stored therein and executable by the processor, the processing instructions operable to, when executed by the processor: determine an amplification gain level applied by the image sensor; determine, based on the amplification gain level, a denoising level and a corresponding sharpening level; and process image data to denoise and sharpen an image corresponding to the image signals using the denoising level and the sharpening level.

42 Claims, 12 Drawing Sheets

(56) References Cited

U.S. PATENT DOCUMENTS

| | | |
|---|---|---|
| 2003/0016856 A1 | 1/2003 | Walker et al. |
| 2008/0239094 A1* | 10/2008 | Baqai .................. H04N 1/00 |
| | | 348/223.1 |
| 2008/0267524 A1 | 10/2008 | Shaked et al. |
| 2008/0285881 A1 | 11/2008 | Gal |
| 2009/0034864 A1 | 2/2009 | Kisilev et al. |
| 2009/0213211 A1 | 8/2009 | Bayer et al. |
| 2011/0216984 A1 | 9/2011 | Tezuka |
| 2012/0294758 A1 | 11/2012 | Avnery |
| 2014/0316283 A1 | 10/2014 | Kaku et al. |
| 2016/0065795 A1 | 3/2016 | Baqai et al. |
| 2016/0239965 A1 | 8/2016 | Kuramoto |
| 2019/0223694 A1 | 7/2019 | Lund et al. |
| 2020/0077969 A1* | 3/2020 | Lee ..................... A61B 6/54 |

OTHER PUBLICATIONS

OmniVision Technologies Inc., Serial Camera Control Bus Functional Specification, 19 pgs., Mar. 2002.
Written Opinion in PCT Application No. PCT/EP2021/062719, dated May 13, 2020, pp. 5.

* cited by examiner

| AD&S VALUE | GAIN | DENOISING VALUE | SHARPENING VALUE |
|---|---|---|---|
| 1 | 0.1 | 1 | 1 |
| 1 | ... | 1 | 1 |
| 1 | 0.9 | 1 | 1 |
| 1 | 1.0 | 1.10 | 0.90 |
| 1 | 1.1 | 1.20 | 0.80 |
| 1 | 1.2 | 1.25 | 0.75 |
| 1 | 1.3 | ... | ... |
| 1 | 1.4 | | |
| 2 | 0.1 | 1.2 | 1 |
| 2 | ... | 1.2 | 1 |
| 2 | 0.9 | 1.2 | 1 |
| 2 | 1.0 | 1.30 | 0.80 |
| 2 | 1.1 | 1.40 | 0.70 |
| 2 | 1.2 | 1.55 | 0.65 |
| 2 | 1.3 | ... | ... |
| 2 | 1.4 | | |
| 3 | 0.1 | | |
| 3 | ... | | |
| 3 | 0.9 | | |
| 3 | 1.0 | | |
| 3 | 1.1 | | |
| 3 | 1.2 | | |
| 3 | 1.3 | | |
| 3 | 1.4 | | |
| 4 | 0.1 | | |
| 4 | ... | | |
| 4 | 0.9 | | |
| 4 | 1.0 | | |
| 4 | 1.1 | | |
| 4 | 1.2 | | |
| 4 | 1.3 | | |
| 4 | 1.4 | | |
| 5 | 0.1 | | |
| 5 | ... | | |

*Fig. 12*

METHOD FOR ADAPTIVE DENOISING AND SHARPENING AND VISUALIZATION SYSTEMS IMPLEMENTING THE METHOD

TECHNICAL FIELD

The disclosure relates to image processing methods and devices. More specifically, the disclosure relates to a method for optimizing images while adaptively suppressing noise during medical procedures.

BACKGROUND OF THE DISCLOSURE

Medical videoscope is a term used herein to broadly denote a medical device having an image sensor configured to obtain images of internal views of a patient. Thus, a videoscope is usable for examination of body openings, e.g. for exploration of a lung cavity. Videoscopes are used in a plurality of procedures and may be sized and shaped specifically for a procedure. Furthermore, a specifically configured device may take its name from the procedure. An endoscope is a videoscope with a steerable distal end. Endoscopes may comprise bronchoscopes, colonoscopes, ear-nose-throat scopes, duodenoscopes, and gastro-intestinal scopes. The term "patient" herein includes humans and animals. Medical monitors can be communicatively coupled to the videoscopes to receive image signals therefrom and present images corresponding to the image signals on an image display of the monitor.

An example endoscope, described in commonly owned U.S. Patent Application No. 2019/0223694, has an insertion tube with an internal working channel and a connector at the handle adapted for the attachment of a syringe. A recess is adapted to accommodate a cylindrical body of the syringe when the syringe is attached to the connector. The endoscope is adapted to perform bronchoalveolar lavage, a procedure for obtaining samples, through the working channel, of organic material from a lung segment of a patient.

A videoscope can also comprise a endobronchial tube with an image sensor, as described in commonly owned U.S. Pat. Nos. 10,321,804 and 10,406,309. The endobronchial tube comprises a tube having a wall, a first inflatable cuff, a second lumen having an open distal end, a second inflatable cuff, a dedicated image sensor lumen in the wall, an image sensor, and an illumination source within the dedicated image sensor lumen at the distal end thereof. The endobronchial tube may include a dedicated cleaning nozzle arrangement embedded in the wall of the tube.

A videoscope can also comprise a endotracheal tube with an image sensor, as described in commonly owned U.S. Pat. No. 10,478,054. The endotracheal tube comprises a tube having a wall defining a ventilation lumen, an image sensor, and an illumination source within a dedicated image sensor lumen at the distal end of the endotracheal tube.

A videoscope can also comprise a video laryngoscope, as described in commonly owned U.S. Pat. No. 9,854,962, known as the King Vision™ aBlade Video Laryngoscope. The video laryngoscope includes a housing including an image display, a battery compartment, and a blade. The blade includes an open channel provided to guide insertion of an endotracheal tube. An image sensor is positioned at a distal end of the blade. The image sensor can be part of the blade or can be connected to the housing and introduced into a cavity of a disposable blade.

Image signals from the videoscopes are processed for presentation of images corresponding to the image signals with an image display. Image processing faces the difficult trade-off between enhancing image details and reducing noise. Due to the random nature of noise, the noise appears as variations in the image that are difficult to discern from image details. Consequently, a system's designer is faced with a trade-off between how much noise to accept vs. the image detail level.

The noise-detail tradeoff is often handled by two processing blocks, or modules, of processing instructions, a denoising block and a sharpening block. The denoising block has the objective of removing noise from the images without compromising the apparent image quality and can operate on either the spatial dimension (image 2D), temporal timension (time average) or both. Traditional spatial and temporal denoising processes may improve images by adding costly computations, such as for example schemes to discern noise from image objects, but are ultimately restricted by the fact that image details and noise are not fully discernable. The sharping block has the objective of enhancing the image detail, thus improving the image quality, without adding too much noise. The two blocks interfere with each other, hence denoising has a tendency to un-sharpen the images while sharping increases noise. The problem is exacerbated as illumination decreases, which taxes the image sensor's image capturing limits, and also when exposure is increased to compensate for low illumination, which may result in unintended motions.

Improved video processing apparatus that can produce a desired image quality even under low light conditions are desired, as are visualization systems comprising the improved video processing apparatus.

SUMMARY OF THE DISCLOSURE

The present disclosure relates to a video processing apparatus and a visualisation system. The video processing apparatus is operable to receive image signals from one or more videoscopes and generate a video stream corresponding to the image signals for presentation with an image display operably coupled to the video processing apparatus. The image display may be combined in a single unit with the video processing apparatus, which in such case may be referred to herein as an "image monitor." The image signals may be analog signals or digital signals comprising image data. The present disclosure further relates to a graphical user interface of such video processing apparatus and processing instructions of such video processing apparatus operable to present images modified based on the image signals.

It is an object of the present disclosure to provide a solution which at least improves the solutions of the prior art. Particularly, it is an object of the present disclosure to provide a graphical user interface for a visualisation system which facilitates and enhances human interaction with the visualization system.

It is a further object of the present disclosure to provide a system and method facilitating enhanced control and usability of a medical visualisation system.

Accordingly, a visualisation system, a video processing apparatus, and a method performed at the video processing apparatus of the visualisation system are disclosed.

In a first aspect, a video processing apparatus (VPA) adapted to receive image signals from a videoscope having an image sensor operable to generate the image signals is provided, the VPA including: a processor; and memory having processing instructions stored therein and executable by the processor, the processing instructions operable to, when executed by the processor: determine an amplification gain level applied by the image sensor; determine, based on the amplification gain level, a denoising level and a corresponding sharpening level; process image data to denoise and sharpen an image corresponding to the image signals using the denosing level and the sharpening level.

The sharpening level and the corresponding denoising level may be configured to generate images with a constant noise level.

A graphical user interface (GUI) module adapted to present a GUI with an image display may be provided, the GUI including an adaptive denoising and sharpening (AD&S) selector operable by a user to select an AD&S level. The processing instructions are operable to determine the denoising level and the corresponding sharpening level based on the amplification gain level and the AD&S level.

For each AD&S level there is a denoising level and a corresponding sharpening level, as a function of the amplification gain.

The AD&S selector may comprise 3, 4, or 5 values.

Preferably, the AD&S selector comprises 5 values, each corresponding to a noise level from a plurality of predetermined noise levels.

A table stored in the memory may comprise values representing denoising and sharpening curves for each of the AD&S values, as a function of the amplification gain.

Processing the image data may further comprise generating video signals corresponding to a sequence of denoised and sharpened images.

The VPA may comprise an output port to communicatively couple the VPA with an image display to present, with the image display, the video signals corresponding to a sequence of denoised and sharpened images.

The VPA may comprise a housing supporting an image display to, with the image display, the video signals corresponding to a sequence of denoised and sharpened images.

The image sensor may comprise an exposure parameter configurable up to a maximum exposure level, and the processing instructions may be operable to determine the denoising level and the corresponding sharpening level: based on the amplification gain level, if the exposure parameter is set to the maximum exposure level, and independently of the amplification gain level, if the exposure parameter is set to less than the maximum exposure level.

The processing instructions may be operable to receive from the image sensor signals including an indication of a level of the exposure parameter.

The processing instructions may be operable to determine the denoising level and the corresponding sharpening level: based on the amplification gain level, if the amplification gain level is greater than a predetermined value, and independently of the amplification gain level, if the amplification gain level is less than the predetermined value. The predetermined value may be a value of the amplification level when an exposure parameter of the image sensor is set at a maximum exposure level. The image sensor may comprise a low-light mode of operation in low light conditions, wherein the processing instructions are operable to determine the denoising level and the corresponding sharpening level: based on the amplification gain level, if the low-light mode of operation is engaged, and independently of the amplification gain level, if the low-light mode of operation is disengaged. The processing instructions may be operable to receive from the image sensor signals including an indication that the low-light mode of operation is engaged.

The processing instructions may be operable to receive from the image sensor signals including an indication of the amplification gain level.

The processing instructions may be operable to transmit an amplification gain level to the image sensor.

The processing instructions may be operable to determine the denoising level and the corresponding sharpening level on a frame basis at a frame-rate slower than a frame-rate of the image sensor.

The processing instructions may be operable to determine the denoising level and the corresponding sharpening level on a frame basis at a frame-rate equal to a frame-rate of the image sensor.

The sharpening level and the corresponding denoising level may be configured to generate images with a noise level that is within a narrow band about a selected noise level.

The processing instructions may include a graphical user interface (GUI) module adapted to present a GUI with a image display, the GUI including an adaptive denoising and sharpening (AD&S) selector operable by a user to select an AD&S level corresponding to one of a plurality of noise levels to thereby select the noise level from the plurality of noise levels. The narrow band may be narrower than +/−20% of the selected noise level.

The narrow band may be narrower than a difference in the noise level of adjacent of the plurality of noise levels.

The processing instructions may be operable to determine the denoising level and the corresponding sharpening level based on the amplification gain level and the AD&S level.

The visualization system may further comprise the videoscope.

In a second aspect, a visualization system is provided, including the VPA of the first aspect.

The visualization system may include the videoscope connectable to the VPA.

The visualization system may include an image display connectable to the VPA.

In a third aspect aspect, method for adaptively sharpening and denoising image data is provided. The method comprises: receiving image signals from a videoscope having an image sensor operable to generate the image signals; determining an amplification gain level applied by the image sensor; determining, based on the amplification gain level, a denoising level and a corresponding sharpening level; and processing image data to denoise and sharpen an image corresponding to the image signals using the denosing level and the sharpening level.

The sharpening level and the corresponding denoising level may be configured to generate images with a constant noise level.

The method may comprise presenting a GUI with an image display, the GUI including an adaptive denoising and sharpening (AD&S) selector operable by a user to select an AD&S level; receiving the AD&S level selected by the user; and determining the denoising level and the corresponding sharpening level based on the amplification gain level and the AD&S level.

For each AD&S level there is a denoising level and a corresponding sharpening level, as a function of the amplification gain.

The AD&S selector may comprise 3, 4, or 5 values.

Preferably, the AD&S selector comprises 5 values, each corresponding to a noise level from a plurality of predetermined noise levels.

The method may comprise reading from a table stored in memory values representing denoising and sharpening curves for each of the AD&S values, as a function of the amplification gain.

The method may comprise generating video signals corresponding to a sequence of denoised and sharpened images, and outputting the video signals in a standard format for presentation with an image display.

The image sensor may comprise an exposure parameter configurable up to a maximum exposure level, and the method may comprise determining the denoising level and the corresponding sharpening level: based on the amplification gain level, if the exposure parameter is set to the maximum exposure level, and independently of the amplification gain level, if the exposure parameter is set to less than the maximum exposure level.

The method may comprise receiving from the image sensor signals including an indication of a level of the exposure parameter.

The method may comprise determining the denoising level and the corresponding sharpening level: based on the amplification gain level, if the amplification gain level is greater than a predetermined value, and independently of the amplification gain level, if the amplification gain level is less than the predetermined value. The predetermined value may be a value of the amplification level when an exposure parameter of the image sensor is set at a maximum exposure level. The image sensor may comprise a low-light mode of operation in low light conditions, wherein the method may comprise determining the denoising level and the corresponding sharpening level: based on the amplification gain level, if the low-light mode of operation is engaged, and independently of the amplification gain level, if the low-light mode of operation is disengaged. The method may comprise receiving from the image sensor signals including an indication that the low-light mode of operation is engaged.

The method may comprise receiving from the image sensor signals including an indication of the amplification gain level.

The method may comprise transmitting an amplification gain level to the image sensor.

The method may comprise determining the denoising level and the corresponding sharpening level on a frame basis at a frame-rate slower than a frame-rate of the image sensor.

The method may comprise determining the denoising level and the corresponding sharpening level on a frame basis at a frame-rate equal to a frame-rate of the image sensor.

The sharpening level and the corresponding denoising level may be configured to generate images with a noise level that is within a narrow band about a selected noise level. The method may comprise receiving with a GUI a user selection of an AD&S level corresponding to one of a plurality of noise levels to thereby select the noise level from the plurality of noise levels. The narrow band may be narrower than +/−20% of the selected noise level.

The narrow band may be narrower than a difference in the noise level of adjacent of the plurality of noise levels.

The method may comprise determining the denoising level and the corresponding sharpening level based on the amplification gain level and the AD&S level.

The different aspects of the present disclosure can be implemented in different ways including methods, image processors, monitors, endoscope systems, and compute program products described above and in the following, each yielding one or more of the benefits and advantages described in connection with at least one of the aspects described above, and each having one or more preferred embodiments corresponding to the preferred embodiments described in connection with at least one of the aspects described above and/or disclosed in the dependent claims. Furthermore, it will be appreciated that embodiments described in connection with one of the aspects described herein may equally be applied to the other aspects.

BRIEF DESCRIPTION OF THE DRAWINGS

The above and/or additional objects, features and advantages of the present disclosure will be further elucidated by the following illustrative and non-limiting detailed description of embodiments, and variations and examples thereof, with reference to the appended drawings, wherein:

FIG. 12 is an example of a table to implement the sharpening and denoising curves of FIGS. 10 and 11;

In the drawings, corresponding reference characters indicate corresponding parts, functions, and features throughout the several views. The drawings are not necessarily to scale and certain features may be exaggerated in order to better illustrate and explain the disclosed embodiments.

DETAILED DESCRIPTION

Figure 1:
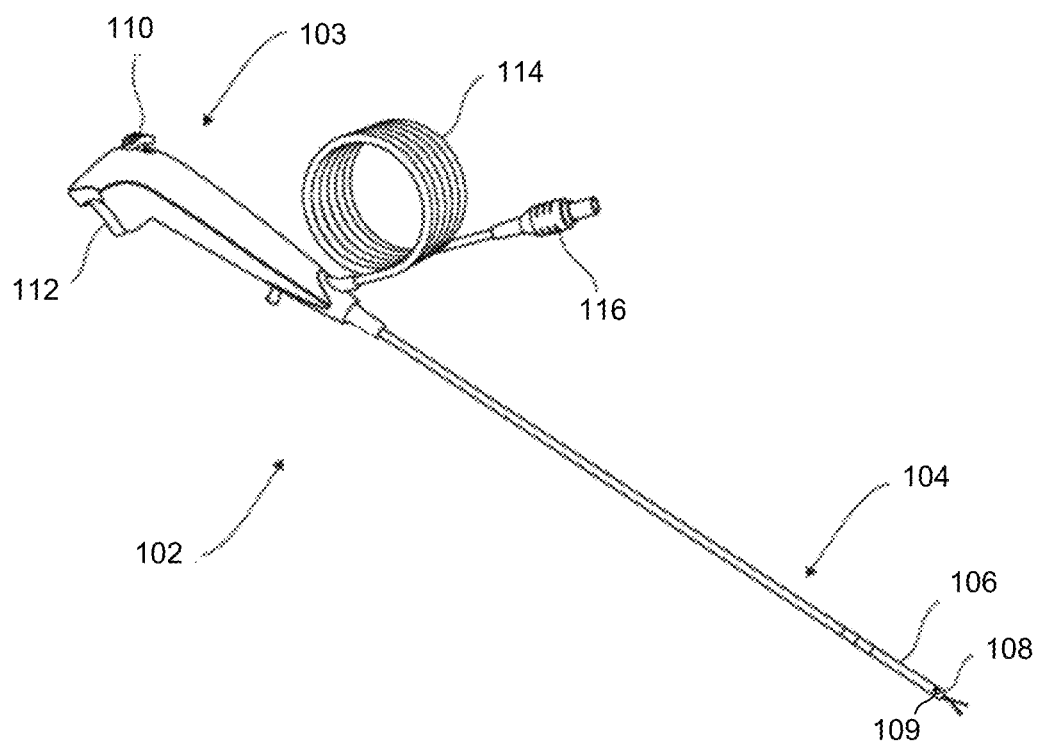
FIG. 1 shows an example of a videoscope.

The balance between image detail and noise is ultimately a user preference. Thus, for a given visualization system, the "optimum" balance can be found through tuning the parameters of the visualization system based on user input to satisfy the user preferences, when the noise levels inherent in the system or the scenes are constant. However, at very low light levels, a method known as "night mode," or "low-light mode," may be used. The low-light mode may activate when the image sensor of the visualization system reaches full exposure time and still does not have enough light to create a desired image. The desired image may be an image that satisfies a minimum average brightness threshold or other optical characteristics. The low-light mode operates as either an analog or digital amplification gain, which multiplies image sensor signals to increase their amplitudes.

But, by amplifying the signals, the low-light mode amplifies both the desired image content and the noise. As gain is increased, the signal to noise ratio decreases. A consequence of using low-light mode in a user-tuned visualization system is that the system may underperform in low light situations.

According to various embodiments described below, the low-light performance of a visualization system is improved by adaptively changing sharpening and denoising as function of the low-light mode amplification.

According to various embodiments described below, the visualization system is improved by adaptively changing sharpening and denoising as function of the amplification gain.

According to various embodiments described below, the visualization system is improved by adaptively changing sharpening and denoising as function of the amplification gain to maintain a level of image noise constant.

In some variations, an amplification gain, or gain, value is provided to denoising and sharpening blocks, and the denoising and sharpening blocks denoise and sharpen images as a function of the gain value. In one example, the denoising and sharpening blocks seek to produce images with substantially constant noise level. Thus, as the gain increases in the low-light mode, the denoising and sharpening blocks seek to counter the resulting increased noise so that the noise remains substantially constant. To maximize the benefits of this approach, the noise level in images captured with bright light, e.g. bright-light mode, when low-light mode inactive, is adjusted to the highest acceptable level, which mitigates the de-sharpening effect of maintaining noise constant during low-light mode. The net effect is that the user does not perceive a change in image quality when the visualization system changes from bright-light to low-light mode. Of course, a noise level less than the highest acceptable level may be applied in bright-light mode.

Often, the low-light mode gain level will be highly correlated with the distance to the scene. Thus, when the user navigates the videoscope and the camera is not near the tissue of interest, a high level of noise may be acceptable because the user is not focused on image details. However, as the camera reaches the tissue of interest, the light source of the camera illuminates the tissue of interest and the low-light mode gain will be reduced, allowing the user to observe fine image details. Thus, a higher level of noise in the navigation mode may be acceptable.

Figure 2A:
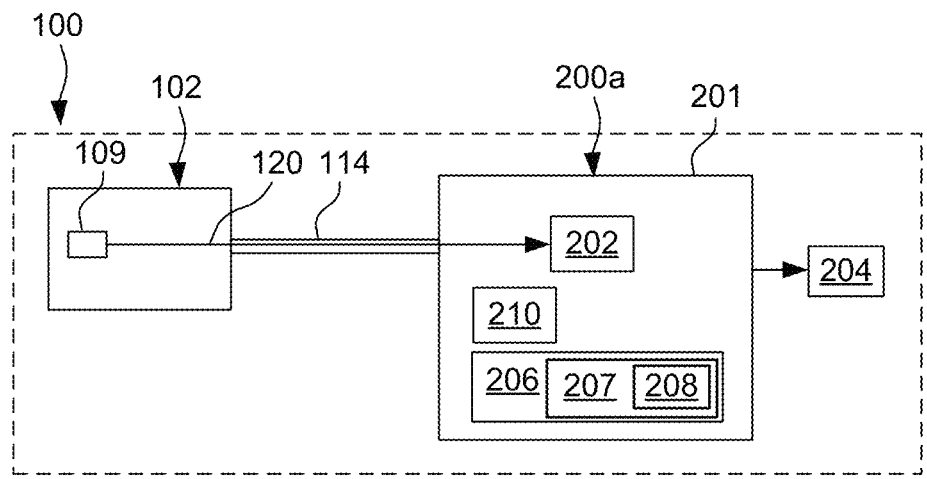
FIGS. 2a and 2b are block diagrams of a visualization system including the videoscope of FIG. 1 and two embodiments of a video processing apparatus.
Figure 2B:
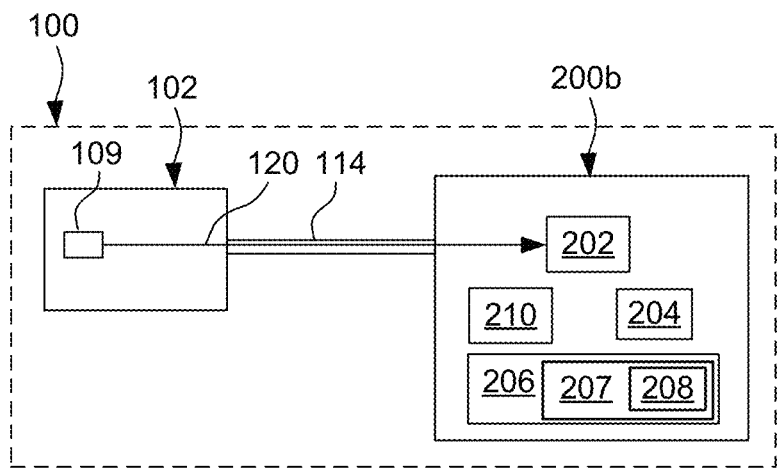

FIGS. 1, 2a and 2b present examples of a visualization system 100, shown in block diagram form in FIGS. 2a and 2b, including a videoscope, illustratively an endoscope 102. Referring to FIG. 1, the endoscope may be adapted for single-use. The endoscope 102 is provided with a handle 103 attached to an insertion tube 104 provided with a bending section 106. The insertion tube 104 and the bending section 106 may be provided with one or several working channels such that instruments, such as a gripping device, may be inserted into the patient via the endoscope. One or several exit holes of the one or several channels may be provided in a tip cap 108. In addition to the exit holes, a camera and one or several light sources, such as light emitting diodes (LEDs), fiber, or any other light emitting devices, may be placed in the tip cap 108. The camera may comprise an image sensor 109, such as a CMOS sensor or any other image capturing device, and one or more lenses defining a field of view of the camera.

The bending section 106 can be steered, e.g. bent in different directions, with respect to the insertion tube 104 to make it possible for the operator to redirect the camera and obtain different views. The operator can control the bending section 106 with a knob 110 placed on the handle 103. The handle is designed so that the knob 110 can be actuated by a thumb of the operator, but other actuation designs to orient the field of view of the camera are also possible. A push button 112 may be used to control a gripping device or other device provided via a working channel. The handle is designed such that the push button 112 can be actuated by a finger of the operator holding the handle, but other tool actuator designs are also possible.

The image signals generated by the camera and, optionally, other data captured by other sensors, can be transferred via a cable 114 having a connector 116 to a video processing apparatus (VPA), examples of which are shown in FIGS. 2a and 2b. Even though wire-based data transmission is illustrated, it is equally possible to transfer image data by using a wireless transceiver supported by the endoscope.

FIGS. 2a and 2b illustrate examples of a VPA 200a, which does not include an image display, and a VPA 200b, which includes an image display. Both figures illustrate a signal conductor 120 extending from the camera through the cable 114 to the VPA 200a, 200b where it is connected to a processor, or central processing unit (CPU), 202. CPU 202 is communicatively coupled with an image display 204, a memory 206 including processing instructions 207 to modify the image data and generate a graphical user interface (GUI) 208, and, optionally, an FPGA 210. FPGA 210 enables rapid start of the VPA 200a, 200b as is needed in medical applications. CPU 202 processes the instructions stored or embedded in the memory 206 to implement an image enhancement method described below with reference to FIGS. 5-17. VPA 200a, 200b comprises a housing 201 at least partially enclosing processor 202, memory 206, and FPGA 210. VPA 200b also comprises image display 204, which is partially enclosed by housing 201.

Processor 202 can include a controller or a processor unit, which may be general purpose or dedicated to the tasks herein, to perform calculations on the image data and control operation of the image display and an interface to communicate with the camera. Digital data of successive image frames are received via line 120. Video data of captured image frames can be outputted by to the memory 206. Processor 202 and memory 206 can each comprise one circuit or a plurality of communicatively connected subcircuits, which may be of the same or different type.

Figure 3:
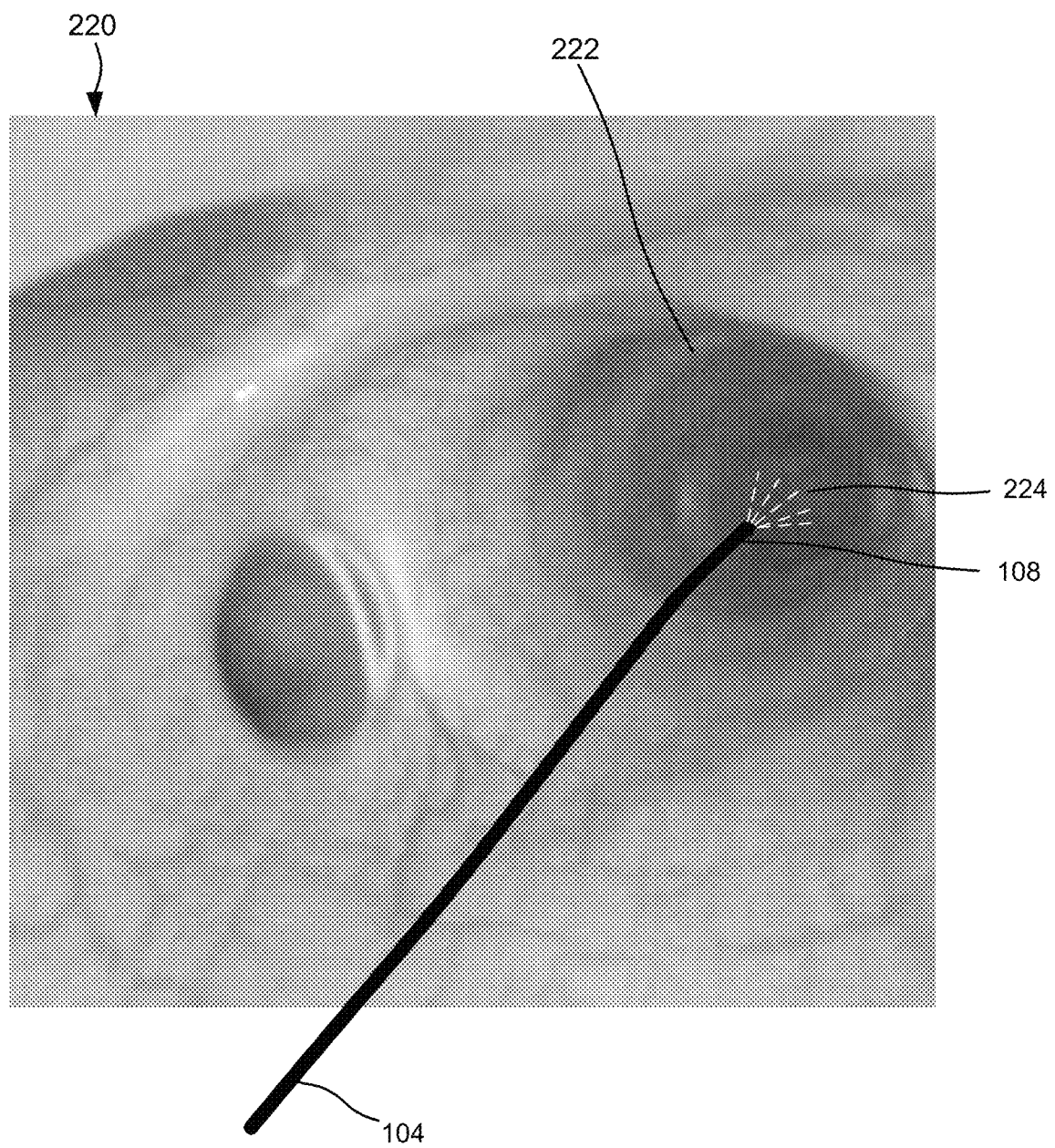
FIG. 3 is a schematic representation of the videoscope of FIG. 1 entering and being navigated into a lung of a patient.

FIG. 3 illustrates a cavity 222 of a lung 220 of a patient. A schematic representation of the insertion tube 104 of the endoscope 102 is shown, including the position of the tip cap 108 and a representation of an illumination pattern 224 provided by a light source in tip cap 108 and corresponding to the field of view of the camera. As can be envisioned, during navigation of the endoscope into the cavity the light source illuminates into the cavity which is sufficient for the purpose of orienting the tip cap 108. Once the endoscope 102 reaches the targeted tissue, the user can steer the tip of the endoscope 102 toward the tissue of interest, the illumination pattern will reflect light from the tissue, and a more detailed image can be obtained, as is desirable, due to the increased reflection of light.

Figure 4:
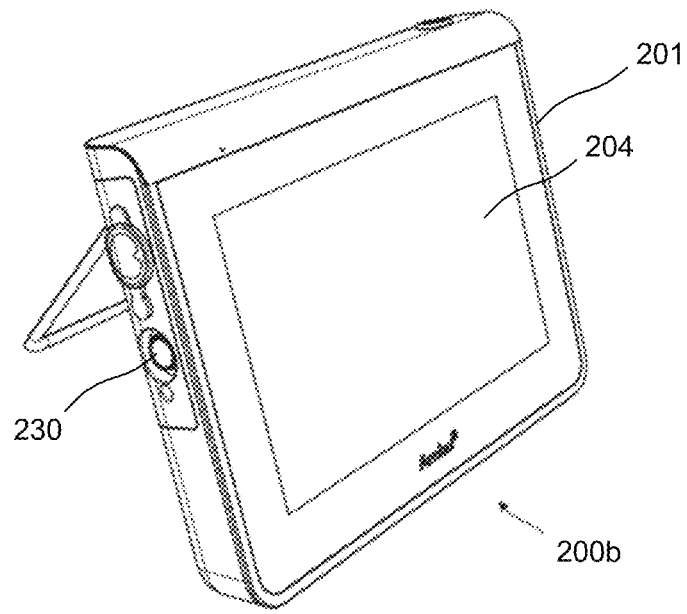
FIG. 4 is a perspective view of an embodiment of the image monitor of FIG. 2.

FIG. 4 is a perspective view of an embodiment of the image monitor 200b including the image display 204 and a communication port 230 operable to receive the connector 116 of the endoscope 102 to establish communications between the image monitor 200b and the endoscope 102. The monitor 200b is configured to display images with the image display 204 of image data captured by the camera of the endoscope 102. An operator of the endoscope 102 is able to see and analyze an inside of the human body to, for instance, localize a position for taking a sample. In addition, the operator will be able to control the instrument in a precise manner due to the visual feedback made available by the image sensor 109 and the image monitor 200b. Further, since some diseases or health issues may result in a shift in natural colors or other visual symptoms, the visual feedback provides the operator valuable input for making a diagnosis based on the image data provided via the camera sensor and the monitor.

The monitor 200b is preferably a re-usable piece of equipment. By having one single-use piece of equipment and another re-usable piece of equipment, most of the data processing capability may be placed in the re-usable piece of equipment in order to reach a cost efficient level at the same time as being safe to use from a health perspective. Single-use devices are not made to withstand sterilization and design considerations include low cost and disposability. The VPA 200a functions as the VPA, or monitor, 200b except that instead of the housing 201 supporting an image display, the images are transmitted through an output port, e.g. an HDMI, VGA, ethernet, or other output signal, for presentation with an image display that may be a remote image display.

Figure 5:
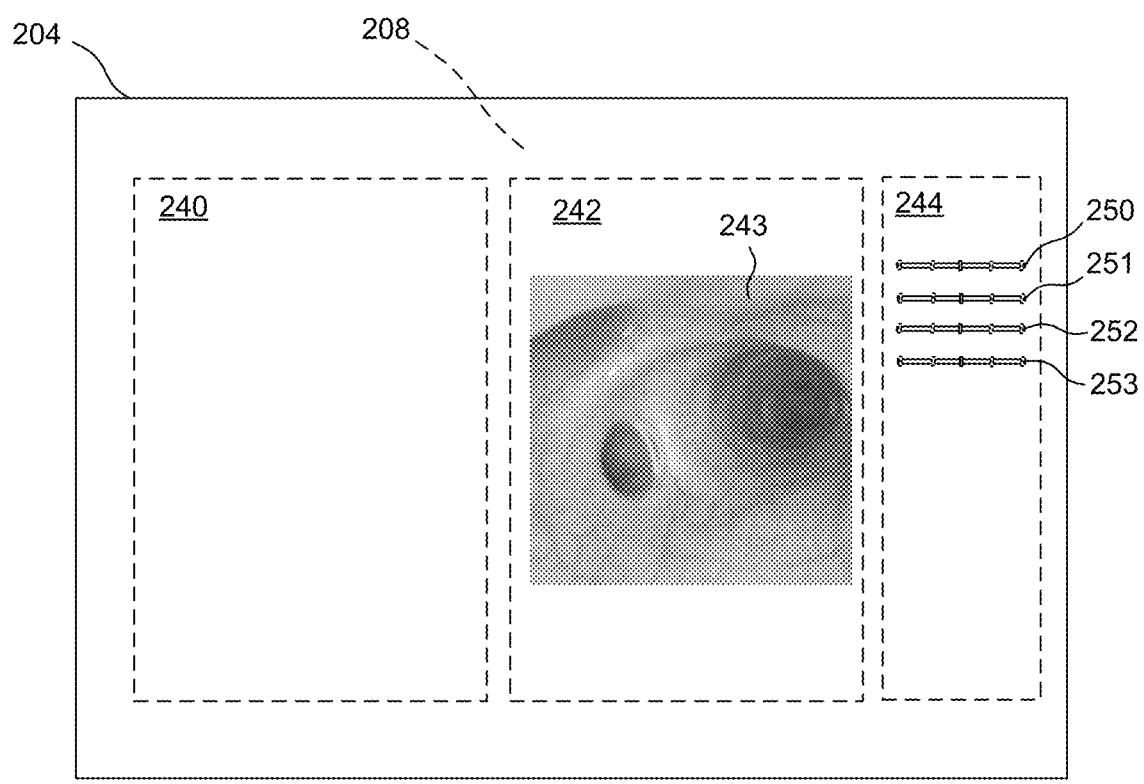
FIG. 5 is a schematic representation of a graphical user interface generated by the video processing apparatus and presented with an image display.

FIG. 5 is a schematic representation of the GUI 208 presented with the image display 204. As shown, the GUI 208 includes a first panel 240, a second panel 242 showing a live view 243 of the images obtained by the camera, and a third panel 244. The presentation of two or more panels and the location or placement of the first, second and third panels is optional. The first panel 240 may be used to present images obtained with additional videoscopes connected to the VPA 200, 200b, or instructions for the user, for example, or to provide control buttons to, for example, capture an image or a portion of the live view for later use. The third panel 244 may be presented at the same time with the live view presentation or can be presented, optionally, to configure the visualization system 100 before the medical procedure begins. The third panel 244, also referred to as the image enhancement control panel 244, includes several enhancement level selectors 250-253. Four enhancement level selectors are shown for the purpose of illustration, which may be assigned to enhance, for example, color, contrast, brightness, and adaptive denoising and sharpening (AD&S). Color, contrast, and brightness function in traditional manners and will not be described further.

In the present embodiment, the adaptive denoising and sharpening level selector 253 comprises a range bar and a knob that the user can move along the range bar to select a level of AD&S. In a preferred embodiment the range bar is programmed to have five AD&S levels. In another embodiment the range bar is programmed to have three AD&S levels. In a further embodiment the range bar is programmed to have a plurality of AD&S levels, e.g. more than five AD&S levels. Buttons, dials, boxes, data input fields, and other known and future developed GUI control types, or physical controls such as potentiometers, dials, etc., can be used set the AD&S level.

Figure 6:
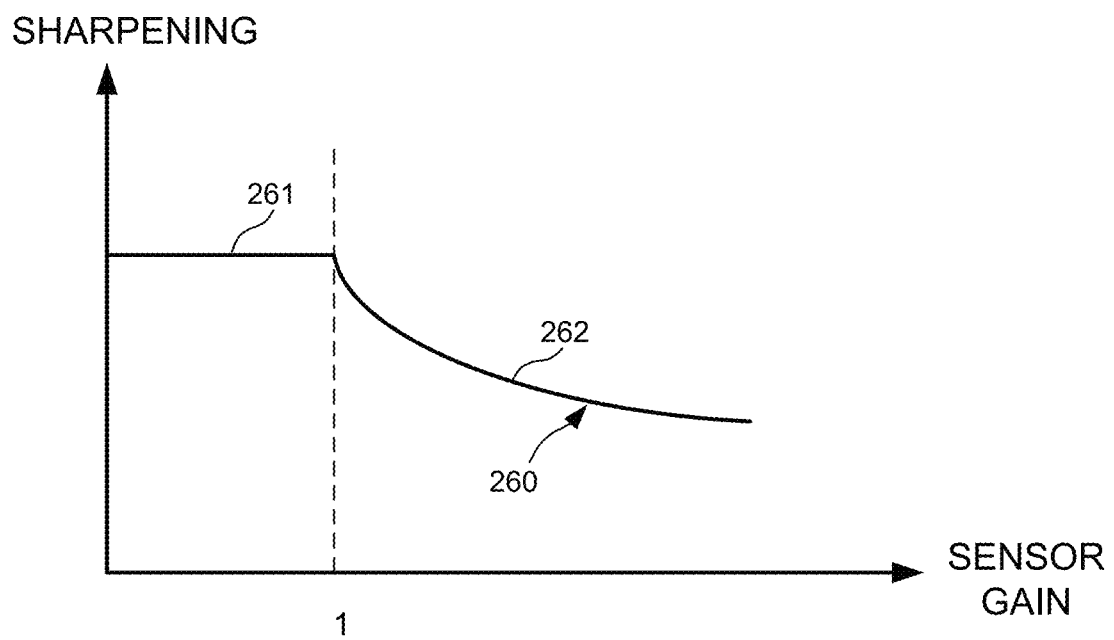
FIGS. 6 and 7 are graphs representing sharpening and denoising curves according with embodiments of the present disclosure.

FIG. 6 is a graph of a sharpening curve 260 including a first, or bright-light, portion 261, and a second, or low-light, portion 262. In the present embodiment, the amount of sharpening decreases as a function of the gain.

Figure 7:
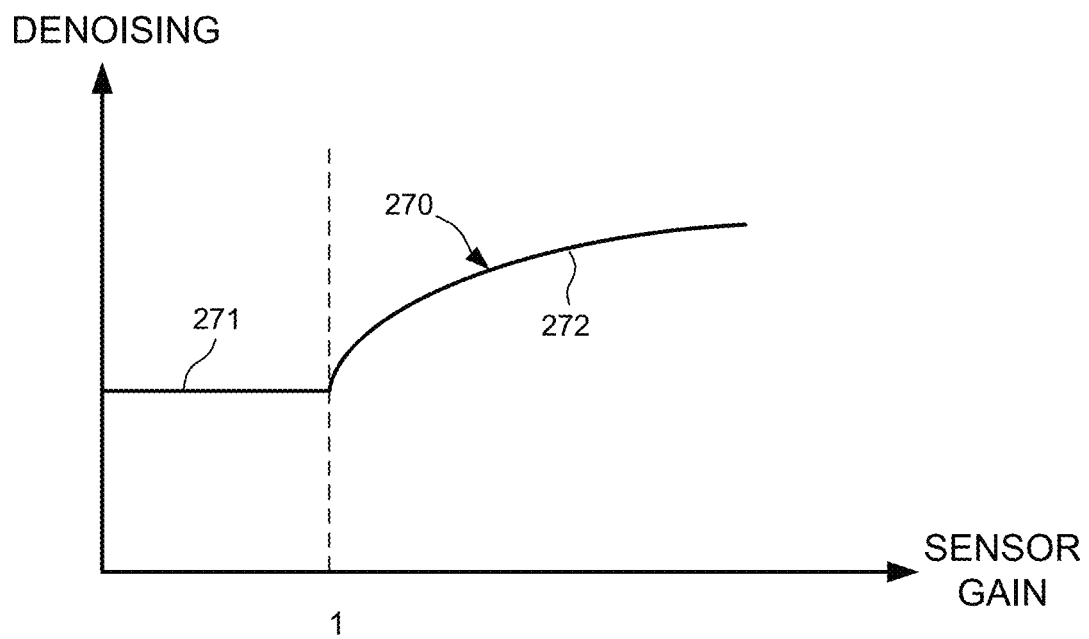
Figure 8:
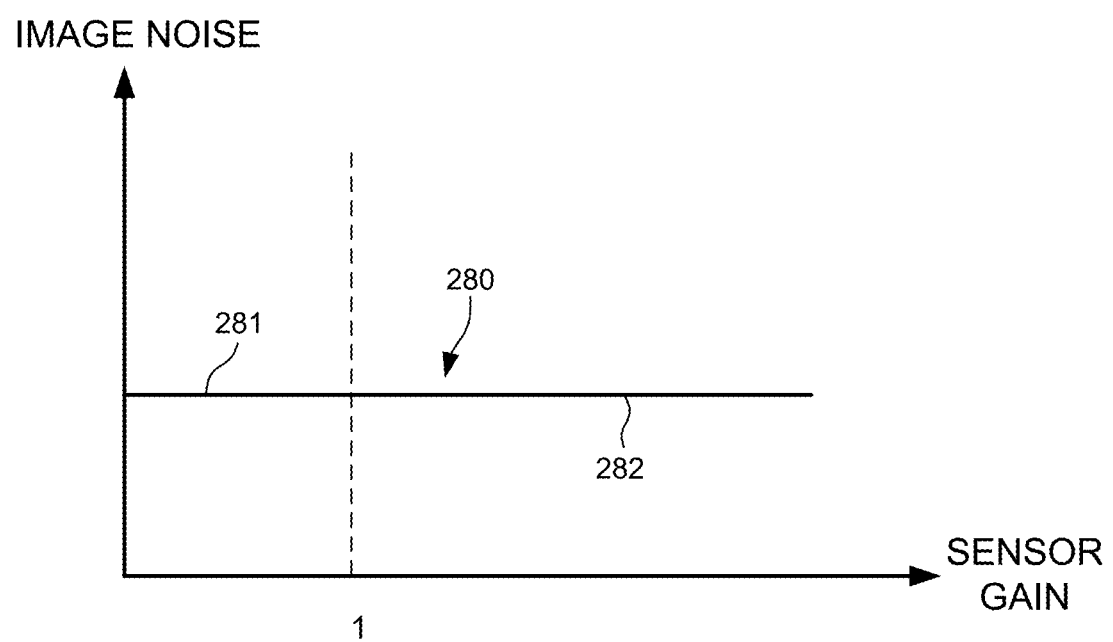
FIG. 8 is a graph representing an ideal noise profile according to embodiments of the present disclosure.

FIG. 7 is a graph of a denoising curve 270 including a first, or bright-light, portion 271, and a second, or low-light, portion 272. In the present embodiment, the amount of denoising increases as a function of the gain. In the present embodiment, sharpening is reduced while simultaneously increasing denoising such that the noise level in the low-light mode is substantially the same as in the bright-light mode. This is shown in FIG. 8, which is a graph of an image noise curve 280 including a first, or bright-light, portion 281, and a second, or low-light, portion 282. It can be seen that image noise is made to be constant in the present embodiment, e.g. first and second portions 281 and 282 form a straight horizontal line. The straight line indicates that a user will see the same amount of noise regarding of lighting conditions. If follows that modifications can be designed that deviate from the constant noise criteria without departing from one of the features of the visualization system, the correspondence of the sharpening and denoising values as a function of amplification gain. Thus, slightly less noise may be programmed during bright-light and low-light modes, for example by adding a slope to curve 280, or by adding curvature to curve 280. Preferably, these modifications will present a continuous and gradual noise increase as exposure and/or gain increase, so as not to be noticeable to the user.

The bright-light portion corresponds to the bright-light mode and the low-light portion corresponds to the low-light mode. In bright-light mode, the level of illumination and exposure are sufficient for the image sensor to obtain a good signal. In low-light mode, the level of illumination and exposure are insufficient for the image sensor to obtain a good signal and the image sensor increases the amplification gain to compensate, increasing noise as explained above.

Some image sensors, for example the Omnivision 6930 image sensor, include automatic exposure control (AEC) and automatic gain control (AGC). The image sensor also includes a serial camera control bus (SCCB) comprising two or three conductors, including a conductor for a clock signal and a conductor for sending and receiving data in a serial manner (illustratively the conductor 120 shown in FIG. 2). An SCCB master circuit is provided in the VPA 200a, 200b to, optionally, control the image sensor and send/receive instructions/data. The AEC and AGC can operate automatically or can be set to a manual mode in which the SCCB controls the exposure and gain. In the automatic mode, the AEC increases exposure until it reaches the exposure upper limit, or maximum exposure. When the maximum exposure is reached, the image sensor increases the gain independently of the VPA 200a, 200b to generate useable images. The image monitor can receive signals indicative of, or including an indication of, the gain. Alternatively, the VPA 200a, 200b can set the image sensor to manual mode, determine that the images are too dark based on a predetermined threshold indicative of sufficient brightness, determine a gain level (for example based on a proportional ratio), and transmit a gain signal to the image sensor to increase the gain.

Figure 9:
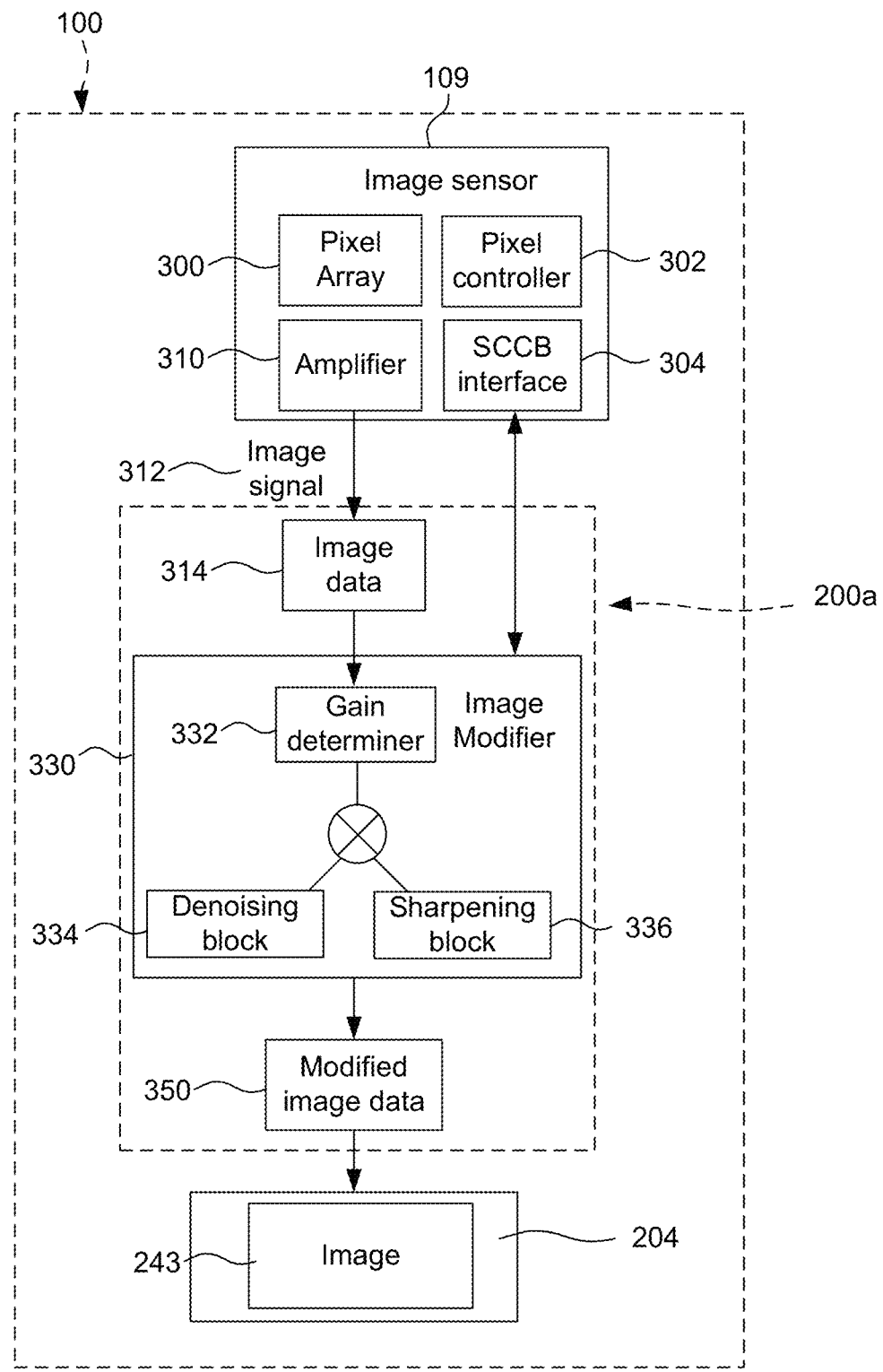
FIG. 9 is a block diagram of another embodiment of a visualization system.

Referring now to FIG. 9, a more detailed block diagram of the visualization system 100 is shown. The image sensor 109 includes a pixel array 300, a pixel controller 302, an amplifier 310, and an SCCB interface 304. The pixel controller 302 may comprise timing and other circuits known in the art to read pixels intensities from the pixel array 300 in a known manner, to process the intensities for the purpose of determining exposure and gain, and for other known purposes. Values of parameters of the image sensor 109 may be transmitted via the SCCB interface 304 to the VPA 200a, 200b. Values of parameters of the image sensor 109 may be transmitted via the SCCB interface 304 from the VPA 200a, 200b to the pixel controller 320 to control the image sensor 109. The image sensor 109 may generate analog or digital image signals 312 representing images captured by the pixel array 300. The image signals 312, if analog, are digitized into image data 314, in a frame-by-frame basis.

The VPA 200a, 200b includes an image modifier module 330 comprised by processing instructions operable to perform various functions. The image modifier module 330 includes a gain determiner module 332, a denoising block 334, and a sharpening block 336. The image data 314 is modified by the image modifier module 330 to generate modified image data 350, which is used to present images 243 with the image display 204.

In some embodiments, the gain determiner module 332 determines the amplification gain by receiving signals from the image sensor 109 comprising an indication of the amplification gain. In other embodiments, the gain determiner module 332 determines the amplification gain, as indicated previously, by processing the image data and determining that the image is to dark, then determining a gain sufficient to brighten the image corresponding to the image data. The gain determiner module 332 may average the intensities of the pixels to determine a brightness level, and determine the gain as a proportion based on a ratio of the brightness level and a brightness threshold.

The denoising block 334 uses a denoising parameter level to more or less aggressively reduce noise in the images. Denoising algorithms are well known, and include spatial domain techniques, in which the image data is manipulated directly, and frequency domain techniques, which manipulate a Fourier transform of the image data. Denoising algorithms are typically based on averaging to produce filters that are subtracted from images and the amount of averaging determines the amount of noise reduction. Typical filters include Gaussian, anisotropic, neighboring, and total variation minimization filters. The present disclosure improves on the use of the techniques by determining the denoising level to be applied by the denoising algorithm, between some predetermined boundaries based on the chosen technique.

The sharpening block 336 uses a sharpening parameter level to more or less aggressively sharpen the images. Sharpening algorithms are well known. In one example, a copy of an image is blurred (e.g. denoised) and a fraction of the deblurred image is subtracted from the original. The result is amplified, thereby enhancing the high frequencies more than the low frequencies and increasing sharpness. Sharpness level can thus be controlled by controlling, for example, the amount of blurring, the fraction to be subtracted, and the amount of amplification. The present disclosure improves on the use of the techniques by determining the sharpening level to be applied by the sharpening algorithm.

As discussed above, in some embodiments, the processing instructions stored in memory are operable to determine, based on the amplification gain level, a denoising level and a corresponding sharpening level; and to process image data to denoise and sharpen an image corresponding to the image signals using the denosing level and the sharpening level. By "corresponding" it is meant that for each denoising level there is a sharpening level, both based on the value of the gain parameter, as depicted by the curves shown in FIGS. 6 and 7. The corresponding values are a set which is a function of the amplification gain and, as described further below, may also be a function of an AD&S value.

In some variations, the sharpening level and the corresponding denoising level are configured to generate images with a constant noise level, as disclosed with reference to FIG. 8. The curves can be constructed empirically, for example by sharpening an image and then denoising it until the noise level matches a desired noise level. Different amounts of denoising and sharpening can be evaluated at various gain levels to choose those that produce, albeit subjectively, good images. Because increased gain increases noise, it can be determined that as gain increases more denoising will be needed which necessarily means less sharpening. Once the desired curves are determined, mathematical models of them can be stored in memory. Alternative, tables with denoising and sharpening values corresponding to various gain levels can be stored in memory. Additionally, mathematical models can be defined and then tested to determine if the variations in noise resulting from the sharpening and denoising are detectable by a user, and if they are not, the models can be stored in memory for execution by the processor. Examples of various curves, and how to generate them, are discussed below with reference to FIGS. 10, 11, and 13-16.

In some embodiments, the image sensor comprises an exposure parameter configurable up to a maximum exposure level, and the processing instructions of the VPA determine the denoising level and the corresponding sharpening level: based on the amplification gain level, if the exposure parameter is set to the maximum exposure level, and independently of the amplification gain level, if the exposure parameter is set to less than the maximum exposure level. Thus, the image sensor may transmit an indication of the exposure level and the processing instructions of the VPA may receive signals including an indication of a level of the exposure parameter, and then utilize the mathematical models or the tables, with the gain value, to set the denoising and sharpening levels if the exposure is at the maximum level. If exposure is less than the maximum level, the denoising and sharpening levels may be constant, as shown in FIGS. 6 and 7 (curve sections 261, 271). Examples of various curves, and how to generate them, are discussed below with reference to FIGS. 10, 11, and 13-16.

In some embodiments, the processing instructions of the VPA determine the denoising level and the corresponding sharpening level: based on the amplification gain level, if the amplification gain level is greater than a predetermined value, and independently of the amplification gain level, if the amplification gain level is less than the predetermined value. The predetermined value may be a value of the amplification level when an exposure parameter of the image sensor is set at a maximum exposure level. The predetermined value may be 1.0. When based on the amplification level, the aforementioned sharpening and denoising curves are used.

In some embodiments, the image sensor comprises a low-light mode of operation, and the processing instructions of the VPA determine the denoising level and the corresponding sharpening level based on the amplification gain level, if the low-light mode of operation is engaged, and independently of the amplification gain level, if the low-light mode of operation is disengaged. The denoising and sharpening levels may be constant if the low-light mode of operation is disengaged. The image sensor may transmit, and the VPA may receive, a low-light mode indication, which the VPA may use to determine how to set denoising and sharpening.

The denoising and sharpening described above, based on the amplification gain, may be performed on a frame basis, e.g. 30 frames-per-second, at a frame-rate equal to or slower than a frame-rate of the image sensor. In other words, the denoising and sharpening values may be determined for each video frame (a video frame is an image) or the values may be used for more than one frame to reduce processing cost. In some embodiments, the denoising and sharpening values, once determined, are used for one, two, three, four, five, or six consecutive frames.

Figure 10:
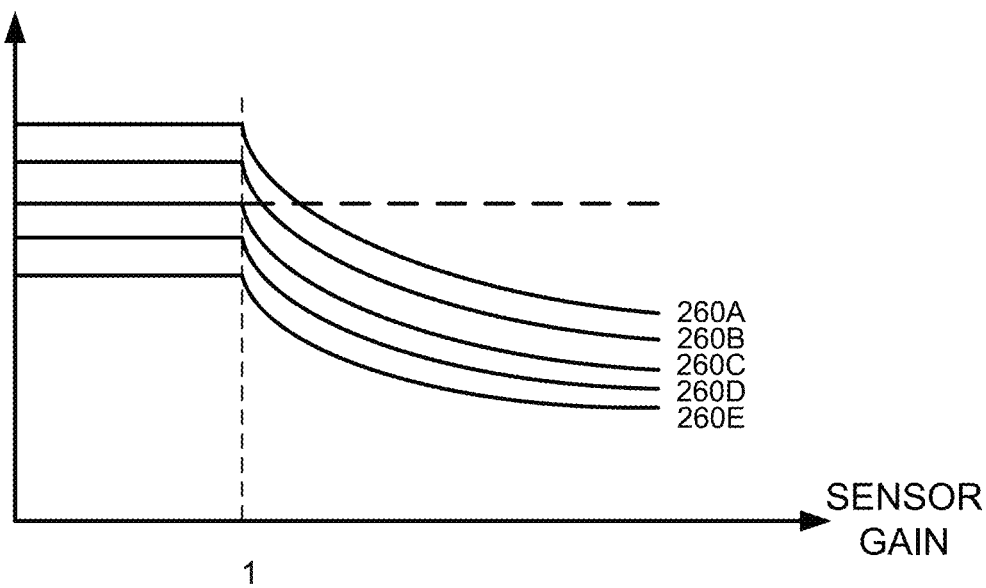
FIGS. 10 and 11 are graphs representing sharpening and denoising curves according with embodiments of the present disclosure.
Figure 11:
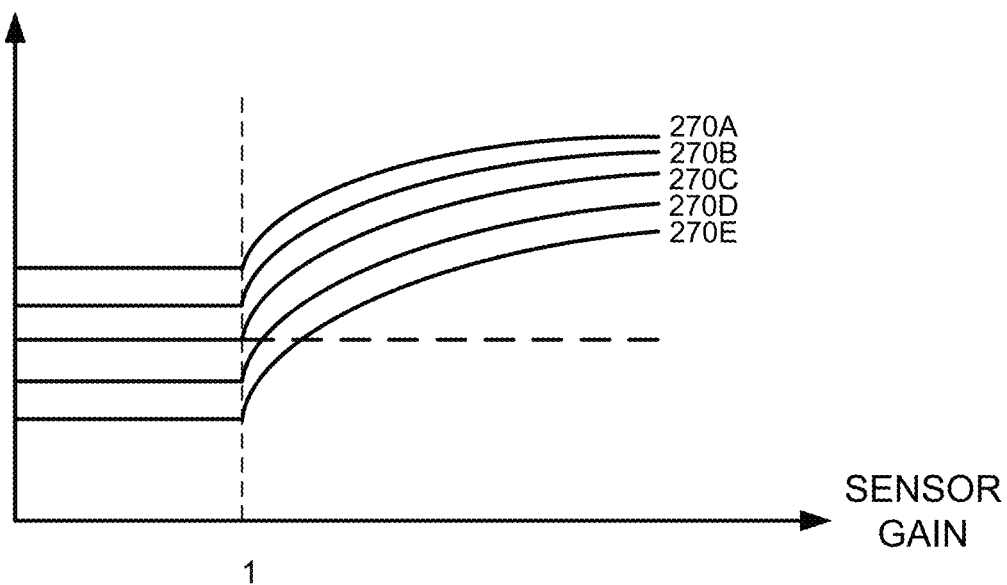

The description of denoising and sharpening functions were described above with respect to one noise level, e.g. see FIG. 8. However, the "best" noise profile is subjective and varies from person to person, therefore to provide an even better visualization system an option is created wherein users can choose a noise level, and then the functions described above are performed with respect to the chosen noise level. The AD&S level selector 253 provides this functionality. A large number of denoising and sharpening curves may be used, with the granularity or resolution of the AD&S level selector 253 determining how large the number can be. However, the differences between adjacent curves may not be meaningful from a practical standpoint until the curves are different enough. In some embodiments, a discrete number of denoising and sharpening curves are provided. The number of denoising (and sharpening) curves may be less than 10, less than 8, less than 6, or less than 4. In a preferred embodiment, the AD&S selector comprises 3, 4, or 5 values, to select 3, 4, or 5 sets of curves (each set including a denoising curve and a sharpening curve). In an even more preferred embodiment, the AD&S selector comprises 5 values, to select 5 sets of curves. An example is shown in FIGS. 10 and 11, in which a user may select with the AD&S level selector 253 a value A-E to select sets of curves 260A & 270A, 260B & 270B, 260C & 270C, 260D & 270D, or 260E & 270E. The first portions of the curves in FIGS. 10 and 11 are uniform (straight with a zero slope) when the amplification gain is less than 1.0 and the second portions are curved according with a second degree polynomial when the amplification gain is greater than 1.0. FIG. 12 shows a table listing the AD&S values, amplification gains, and corresponding denoising and sharpening values. The amplification gains, and corresponding denoising and sharpening values, are arbitrary numbers shown only to illustrate the structure of the table.

Figure 13:
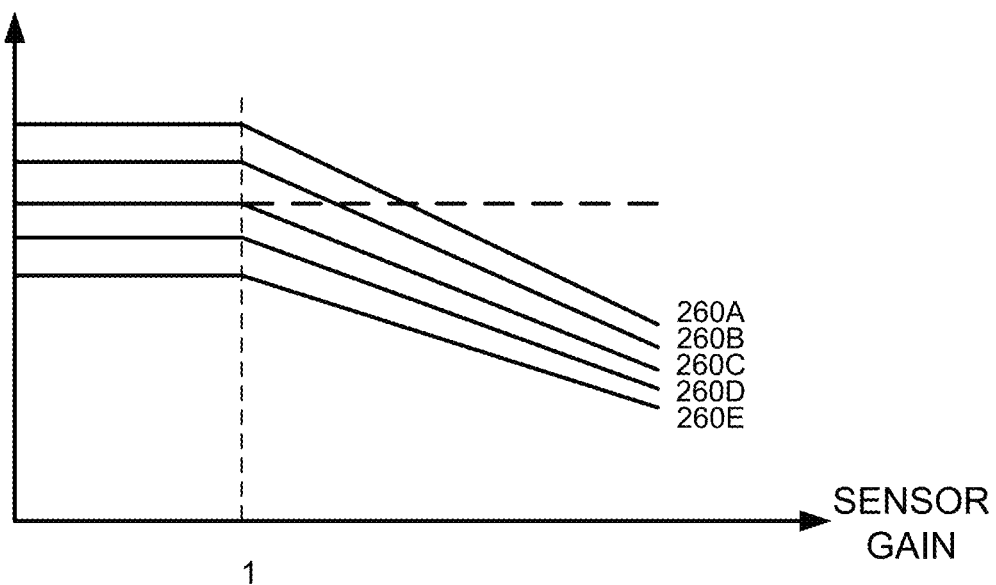
FIGS. 13 and 14 are graphs representing additional examples of sharpening and denoising curves according with embodiments of the present disclosure.
Figure 14:
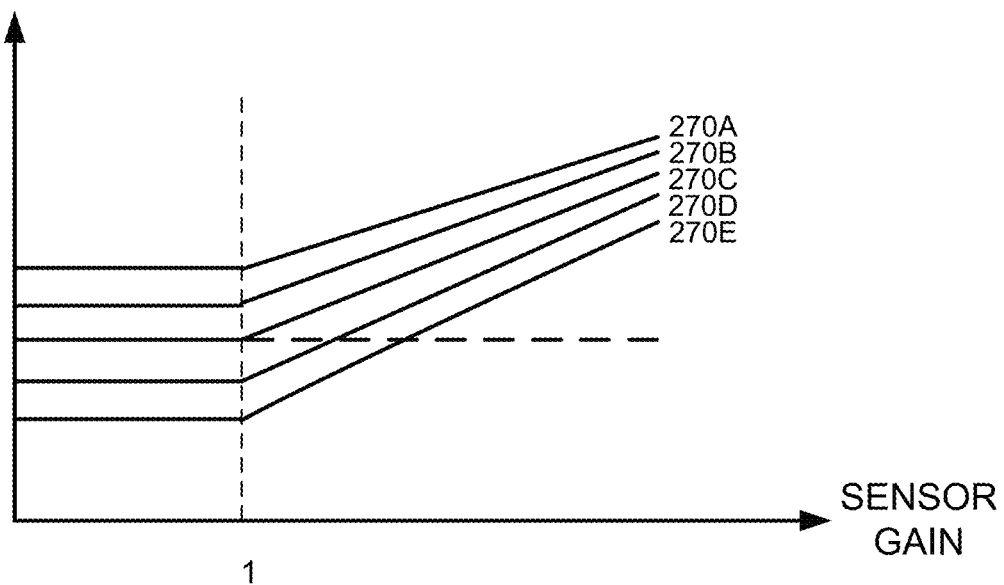

Another example is shown in FIGS. 13 and 14, in which the first portions of the curves (amplification gain<1.0) are uniform and the second portions (amplification gain>1.0) are straight with a slope different than zero. The second portions of the curves are simpler versions of those presented in FIGS. 10 and 11 from the standpoint that it is easier to model a straight line than a curved line. Simpler modeling might be appropriate if the system lacks the resources to store a fine-resolution table, such that a mathematical model is needed instead. Additionally, it may be simpler to determine the slopes. In one example, the largest slopes possible are used that do not negatively affect (subjectively) the images. This can be accomplished by trying a too-large (absolute value) sharpening slope and then reducing the slope (absolute value) until the negative effects are substantially mitigated. Denoising is then applied to achieve the selected noise level. In another example, images taken at maximum amplification gain are sharpened using the sharpening block until the images are subjectively adequate. The denoising block is then used to denoise the images until they achieve the predetermined noise level (selected from A-E). The sharpening and denoising values used to obtain the final image are the values at the maximum amplification gain, e.g. the last points on curves 260A-E and 270A-E. With these values the straight lines can be drawn. In one variation, the slopes for one of the sets are determined, and the same slopes are used for all the sets, with different Y-axis values. This further reduces the computational cost and thus reduces the cost of the VPA.

The curves in FIGS. 10 and 11 can be generated in a similar manner, except that in addition to the last point (maximum amplification gain) an intermediate point (between gain=1.0 and gain=maximum) is needed to fit the second degree polynomial. As expected, curve 260A exhibits the most sharpening and corresponds with curve 270 which exhibits the most denoising. Since sharpening blurs, it makes sense that additional denoising would be needed. The alternative methods described above can be used as well, such as, for example defining a curve and then testing it to see if the visual effect is noticeable or poor. Additionally, once a curve is defined, the model can be used by simply changing the value corresponding to the Y-axis.

Figure 15:
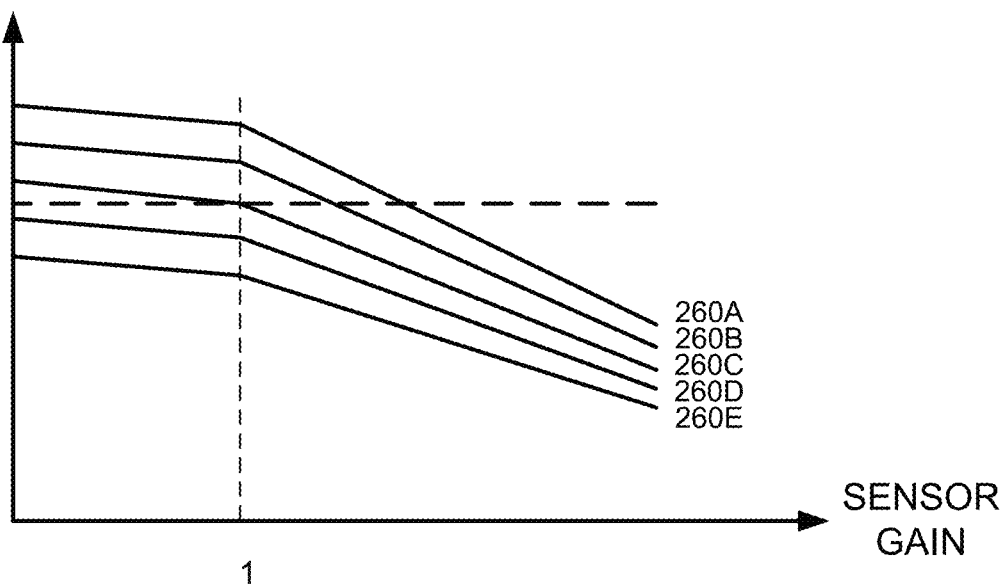
FIGS. 15 and 16 are graphs representing yet additional examples of sharpening and denoising curves according with embodiments of the present disclosure.
Figure 16:
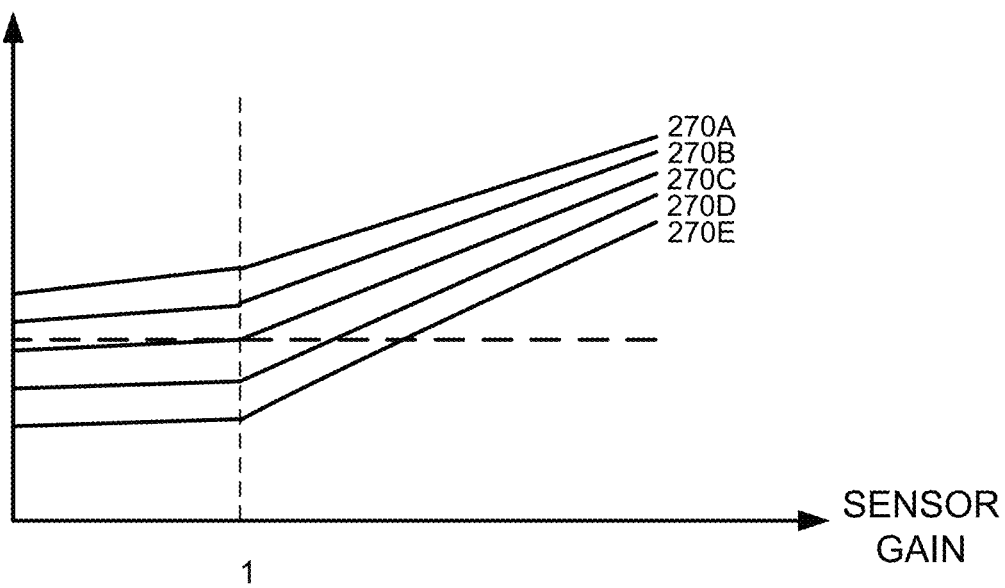

Another example is shown in FIGS. 15 and 16, in which the first portions of the curves are also straight and sloped. These first portions address the noise that is introduced when the exposure is increased, which is a motion-based noise. Denoising is increased to compensate for the increased exposure (moving from left to right toward gain=1.0). However, because this source of noise has a smaller effect than the noise resulting from increased gain, the slopes are less aggressive. Thus, the absolute values of the slopes of the second portions are greater than the absolute values of the slopes of the first portions. The first portions in FIGS. 10, 11, and 13-16 could also be curved in accord with a second degree polynomial, following the principles described above, mainly that the curvature of the first portions is less aggressive than the curvature of the second portions in FIGS. 10 and 11, to compensate for motion noise but not the same degree as the compensation for increased gain.

Figure 17:
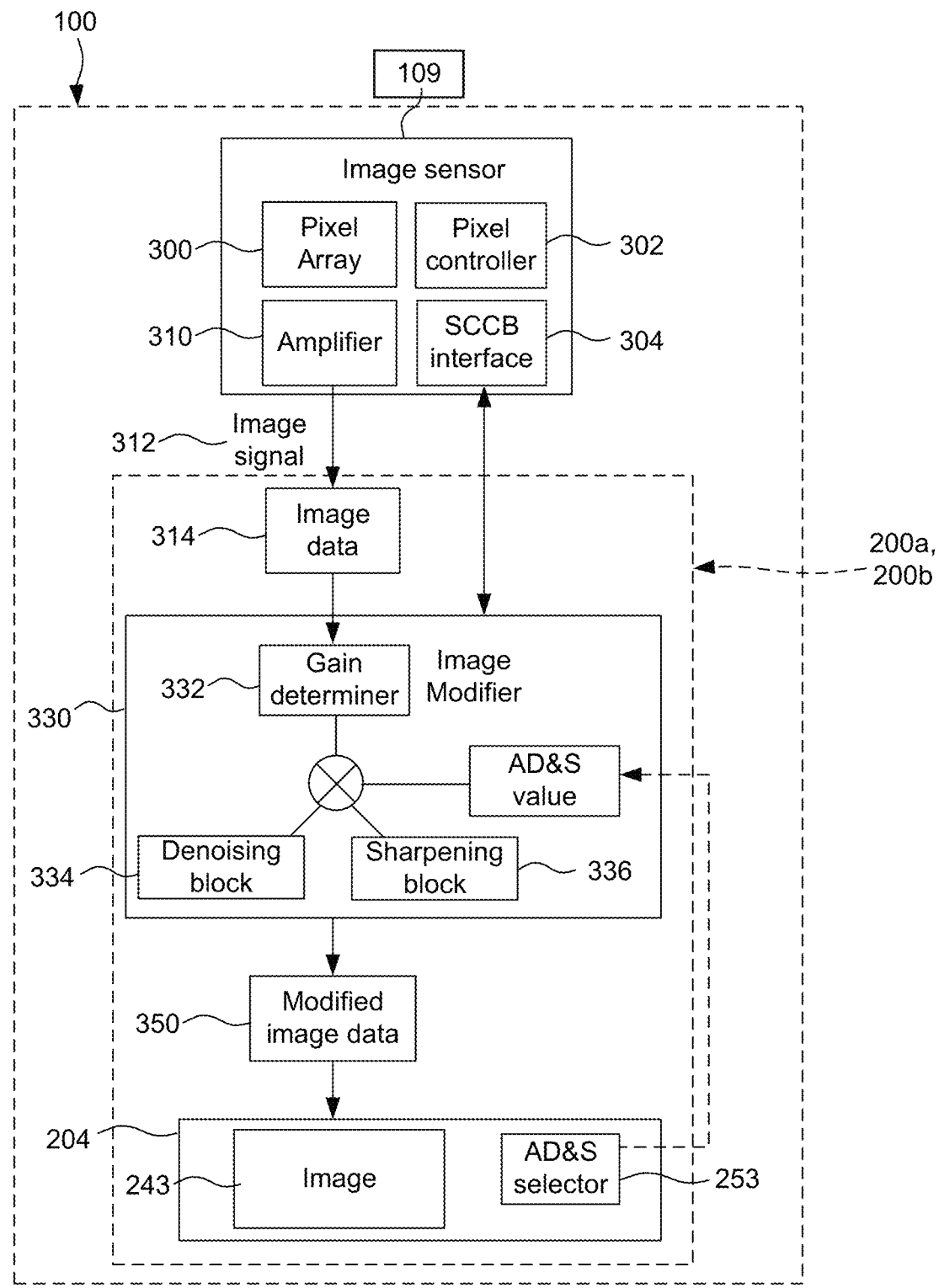
FIG. 17 is a block diagram of yet another embodiment of a visualization system.

The image display may be a touch screen. In some embodiments, the processing instructions include the GUI module operable to provide the GUI with the image display. The GUI includes the AD&S selector. The processing instructions are operable to determine the denoising level and the corresponding sharpening level based on not only the amplification gain level, but also the AD&S level, as discussed above. The AD&S level selects the set of curves from a predetermined plurality of curves, and then the amplification gain level is used with the selected curves in the same manner described above with reference to FIGS. 6-9. Referring now to FIG. 17, a more detailed block diagram of the visualization system 100 is shown, showing the AD&S level selector 253 presented with image display 204 and the AD&S value being used by the image modifier module 330 to determine the denoising and sharpening values.

In another aspect, a method of processing images is provided. The method is operable in a visualization system comprising a videoscope coupled to a VPA. The VPA is adapted to receive image signals from the videoscope, having an image sensor operable to generate the image signals. The method comprises: determining an amplification gain level applied by the image sensor; determining, based on the amplification gain level, a denoising level and a corresponding sharpening level; and processing image data to denoise and sharpen an image corresponding to the image signals using the denosing level and the sharpening level.

The sharpening level and the corresponding denoising level may be configured to generate images with a constant noise level.

The sharpening level and the corresponding denoising level may be configured to generate images with a noise level not to exceed a predetermined noise threshold. The predetermined noise threshold may be selected by the user from a plurality of AD&S values. Additionally, the sharpening level and the corresponding denoising level may be configured to generate images with a noise level that is equal to or greater than a predetermined fraction of the predetermined noise threshold. In one example, the predetermined fraction is 0.9. In another example, the predetermined fraction is 0.8. In a further example, the predetermined fraction is 0.7. Thus, the curves are configured to, for example, generate images with noise between 80%-100% of the noise corresponding to the selected AD&S value.

The sharpening level and the corresponding denoising level may be configured to generate images with a noise level within a narrow noise band about a predetermined noise threshold. The predetermined noise threshold may be selected by the user from a plurality of AD&S values. In one example, the noise band may be 10%, 20% or 30% of the predetermined noise threshold. Thus, the curves are configured to, for example, generate images with noise between −15% and +15% of the noise level corresponding to the selected AD&S value.

The method may comprise selecting, with a GUI including an AD&S selector, an AD&S level. The method may also comprise determining the denoising level and the corresponding sharpening level based on the amplification gain level and the AD&S level. For each AD&S level there may be a denoising level and a corresponding sharpening level, as a function of the amplification gain. The AD&S selector may comprise 3, 4, or 5 values. More preferably, the AD&S selector may comprise 5 values.

A table may be stored in memory comprising values representing denoising and sharpening curves for each of the AD&S values, as a function of the amplification gain. The method may comprise receiving an indication of the amplification gain level, and reading the table to determine the denoising and sharpening values.

The method may comprise determining the denoising level and the corresponding sharpening level based on the amplification gain level or independently of the amplification gain level based on (a) the exposure parameter set to the maximum exposure level, or not, (b) exposure being greater or less than a predetermined value, or (c) if a low-light mode of operation is engaged, or disengaged.

The method may comprise receiving indications of exposure values or low-light mode engagement, and an indication of the amplification gain level.

The method may also comprise providing the denoising level and the sharpening level to the sharpening block of processing instructions and to the denoising block of processing instructions to effect the sharpening and denoising.

While this disclosure has been described as having exemplary designs, this application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

While a particular feature of the invention may have been disclosed with respect to only one of several implementations, such feature may be combined with one or more other features of the other implementations as may be desired and advantageous for any given or particular application.

The Abstract of the disclosure is provided to comply with 37 C.F.R. 1.72(b), requiring an abstract that will allow the reader to quickly ascertain the nature of the technical disclosure. It is submitted with the understanding that it will not be used to interpret or limit the scope or meaning of the claims.

We claim:

1. A visualization system comprising:
    a video processing apparatus (VPA) adapted to receive image signals from a videoscope having an image sensor configured to generate the image signals, the VPA including:
    a processor; and
    memory having processing instructions stored therein and executable by the processor, the processing instructions configured to, when executed by the processor:
        determine an amplification gain level applied by the image sensor;
        determine, based on the amplification gain level, a denoising level and a corresponding sharpening level; and
        process image data to denoise and sharpen an image corresponding to the image signals using the denosinq level and the sharpening level,
    wherein the image sensor comprises an exposure parameter configurable up to a maximum exposure level, and wherein the processing instructions are configured to determine the denoising level and the corresponding sharpening level:
    based on the amplification gain level, if the exposure parameter is set to the maximum exposure level, and
    independently of the amplification gain level, if the exposure parameter is set to less than the maximum exposure level.

2. The visualization system of claim 1, wherein the sharpening level and the corresponding denoising level are configured to generate images with a constant noise level.

3. The visualization system of claim 1, wherein the processing instructions include a graphical user interface (GUI) module adapted to present a GUI with an image display, the GUI including an adaptive denoising and sharpening (AD&S) selector operable by a user to select an AD&S level.

4. The visualization system of claim 3, wherein the processing instructions are operable to determine the denoising level and the corresponding sharpening level based on the amplification gain level and the AD&S level.

5. The visualization system of claim 4, wherein for each AD&S level there is a denoising level and a corresponding sharpening level, as a function of the amplification gain.

6. The visualization system of claim 3, wherein the AD&S selector comprises 5 values.

7. The visualization system of claim 1, wherein the processing instructions are operable to receive from the image sensor signals including an indication of a level of the exposure parameter.

8. The visualization system of claim 1, wherein the sharpening level and the corresponding denoising level are configured to generate images with a noise level that is within a narrow band about a selected noise level.

9. The visualization system of claim 8, wherein the processing instructions include a graphical user interface (GUI) module adapted to present a GUI with an image display, the GUI including an adaptive denoising and sharpening (AD&S) selector operable by a user to select an AD&S level corresponding to one of a plurality of noise levels to thereby select the noise level from the plurality of noise levels.

10. The visualization system of claim 9, wherein the processing instructions are operable to determine the denoising level and the corresponding sharpening level based on the amplification gain level and the AD&S level.

11. The visualization system of claim 1, further comprising the videoscope.

12. A visualization system comprising:
a video processing apparatus (VPA) adapted to receive image signals from a videoscope having an image sensor configured to generate the image signals, the VPA including:
a processor; and
memory having processing instructions stored therein and executable by the processor, the processing instructions configured to, when executed by the processor:
determine an amplification gain level applied by the image sensor;
determine, based on the amplification gain level, a denoising level and a corresponding sharpening level; and
process image data to denoise and sharpen an image corresponding to the image signals using the denoising level and the sharpening level,
wherein the processing instructions are configured to determine the denoising level and the corresponding sharpening level:
based on the amplification gain level, if the amplification gain level is greater than a predetermined value, and
independently of the amplification gain level, if the amplification gain level is less than the predetermined value, and
wherein the predetermined value is a value of the amplification level when an exposure parameter of the image sensor is set at a maximum exposure level.

13. The visualization system of claim 12, wherein the sharpening level and the corresponding denoising level are configured to generate images with a constant noise level.

14. The visualization system of claim 12, wherein the processing instructions include a graphical user interface (GUI) module adapted to present a GUI with an image display, the GUI including an adaptive denoising and sharpening (AD&S) selector operable by a user to select an AD&S level.

15. The visualization system of claim 14, wherein the processing instructions are operable to determine the denoising level and the corresponding sharpening level based on the amplification gain level and the AD&S level.

16. The visualization system of claim 15, wherein for each AD&S level there is a denoising level and a corresponding sharpening level, as a function of the amplification gain.

17. The visualization system of claim 14, wherein the AD&S selector comprises 5 values.

18. The visualization system of claim 12, further comprising the videoscope.

19. The visualization system of claim 12, wherein the processing instructions include a graphical user interface (GUI) module adapted to present a GUI with an image display, the GUI including an adaptive denoising and sharpening (AD&S) selector operable by a user to select an AD&S level corresponding to one of a plurality of noise levels to thereby select the noise level from the plurality of noise levels.

20. The visualization system of claim 19, wherein the processing instructions are operable to determine the denoising level and the corresponding sharpening level based on the amplification gain level and the AD&S level.

21. A method to adaptively sharpen and denoise image data, the method comprising:
receiving, by a video processing apparatus (VPA), image signals from a videoscope having an image sensor configured to generate the image signals, the VPA including a processor and a memory, the memory having processing instructions stored therein and executable by the processor, the processing instructions configured to, when executed by the processor:
determine an amplification gain level applied by the image sensor;
determine, based on the amplification gain level, a denoising level and a corresponding sharpening level; and
process image data to denoise and sharpen an image corresponding to the image signals using the denoising level and the sharpening level,
wherein the image sensor comprises an exposure parameter configurable up to a maximum exposure level, and
wherein the processing instructions are configured to determine the denoising level and the corresponding sharpening level;
based on the amplification gain level, if the exposure parameter is set to the maximum exposure level, and
independently of the amplification gain level, if the exposure parameter is set to less than the maximum exposure level.

22. The method of claim 21, wherein the sharpening level and the corresponding denoising level are configured to generate images with a constant noise level.

23. The method of claim 21, wherein the processing instructions are operable to:
present with an image display a graphical user interface (GUI) including an adaptive denoising and sharpening (AD&S) selector operable by a user to select an AD&S level;
receive the AD&S level selected by the user; and
determine the denoising level and the corresponding sharpening level based on the amplification gain level and the AD&S level.

24. The method of claim 23, wherein for each AD&S level there is a denoising level and a corresponding sharpening level, as a function of the amplification gain.

25. The method of claim 23, wherein the AD&S selector comprises 5 values, each corresponding to a noise level from a plurality of predetermined noise levels.

26. The method of claim 21, wherein the sharpening level and the corresponding denoising level are configured to generate images with a noise level that is within a narrow band about a selected noise level.

27. The method of claim 26, wherein the narrow band is narrower than +/−20% of the selected noise level.

28. The method of claim 21, wherein the sharpening level and the corresponding denoising level are configured to generate images with a constant noise level.

29. The method of claim 21, wherein the sharpening level and the corresponding denoising level are configured to generate images with a noise level that is within a narrow band about a selected noise level.

30. The method of claim 21, wherein the processing instructions are operable to receive from the image sensor signals including an indication of a level of the exposure parameter.

31. The method of claim 21, wherein the processing instructions are operable to:
present with an image display a graphical user interface (GUI) including an adaptive denoising and sharpening (AD&S) selector operable by a user to select an AD&S level;

receive the AD&S level selected by the user; and determine the denoising level and the corresponding sharpening level based on the amplification gain level and the AD&S level.

32. The method of claim 31, wherein for each AD&S level there is a denoising level and a corresponding sharpening level, as a function of the amplification gain.

33. The method of claim 32, wherein the AD&S selector comprises 5 values, each corresponding to a noise level from a plurality of predetermined noise levels.

34. The method of claim 21, wherein the processing instructions include a graphical user interface (GUI) module adapted to present a GUI with an image display, the GUI including an adaptive denoising and sharpening (AD&S) selector operable by a user to select an AD&S level corresponding to one of a plurality of noise levels to thereby select the noise level from the plurality of noise levels.

35. A method to adaptively sharpen and denoise image data, the method comprising:

receiving, by a video processing apparatus (VPA), image signals from a videoscope having an image sensor configured to generate the image signals, the VPA including a processor and a memory, the memory having processing instructions stored therein and executable by the processor, the processing instructions configured to, when executed by the processor:

determine an amplification gain level applied by the image sensor;

determine, based on the amplification gain level, a denoising level and a corresponding sharpening level; and process image data to denoise and sharpen an image corresponding to the image signals using the denosing level and the sharpening level, wherein the processing instructions are configured to determine the denoising level and the corresponding sharpening level:

based on the amplification gain level, if the amplification gain level is greater than a predetermined value, and independently of the amplification gain level, if the amplification gain level is less than the predetermined value, wherein the predetermined value is a value of the amplification level when an exposure parameter of the image sensor is set at a maximum exposure level.

36. The method of claim 35, wherein the sharpening level and the corresponding denoising level are configured to generate images with a constant noise level.

37. The method of claim 35, wherein the sharpening level and the corresponding denoising level are configured to generate images with a noise level that is within a narrow band about a selected noise level.

38. The method of claim 35, wherein the processing instructions are operable to receive from the image sensor signals including an indication of a level of the exposure parameter.

39. The method of claim 35, wherein the processing instructions are operable to:

present with an image display a graphical user interface (GUI) including an adaptive denoising and sharpening (AD&S) selector operable by a user to select an AD&S level;

receive the AD&S level selected by the user; and determine the denoising level and the corresponding sharpening level based on the amplification gain level and the AD&S level.

40. The method of claim 39, wherein for each AD&S level there is a denoising level and a corresponding sharpening level, as a function of the amplification gain.

41. The method of claim 40, wherein the AD&S selector comprises 5 values, each corresponding to a noise level from a plurality of predetermined noise levels.

42. The method of claim 35, wherein the processing instructions include a graphical user interface (GUI) module adapted to present a GUI with an image display, the GUI including an adaptive denoising and sharpening (AD&S) selector operable by a user to select an AD&S level corresponding to one of a plurality of noise levels to thereby select the noise level from the plurality of noise levels.

\* \* \* \* \*